United States Patent
Iglesias

(10) Patent No.: US 12,263,006 B2
(45) Date of Patent: Apr. 1, 2025

(54) TREATMENT OF MALE URINARY INCONTINENCE AND SEXUAL DYSFUNCTION

(71) Applicant: Remendium Labs LLC, Baton Rouge, LA (US)

(72) Inventor: Ramon Jose Iglesias, DeLeon Springs, FL (US)

(73) Assignee: Axena Health, Inc., Auburndale, MA (US)

( * ) Notice: Subject to any disclaimer, the term of this patent is extended or adjusted under 35 U.S.C. 154(b) by 478 days.

(21) Appl. No.: 17/129,526

(22) Filed: Dec. 21, 2020

(65) Prior Publication Data

US 2021/0145353 A1  May 20, 2021

Related U.S. Application Data

(63) Continuation of application No. 15/627,292, filed on Jun. 19, 2017, now abandoned, which is a
(Continued)

(51) Int. Cl.
*A61B 5/00* (2006.01)
*A61B 5/20* (2006.01)
*A61B 5/22* (2006.01)

(52) U.S. Cl.
CPC .......... *A61B 5/4393* (2013.01); *A61B 5/0036* (2018.08); *A61B 5/205* (2013.01);
(Continued)

(58) Field of Classification Search
CPC .............. A61M 25/0017; A61M 25/10; A61M 2025/0002; A61M 2202/0014;
(Continued)

(56) References Cited

U.S. PATENT DOCUMENTS 2,830,582 A    4/1958  Ljung
3,854,476 A    12/1974 Dickinson, III et al.
(Continued)

FOREIGN PATENT DOCUMENTS

CA   2625428 A1   7/2007
CA   2862928 A1   8/2013
(Continued)

OTHER PUBLICATIONS

Glazer et al., "Pelvic floor muscle biofeedback in the treatment of urinary incontinence: A literature review," Appl Psychophysiol Biofeedback. 31(3):187-201 (2006) (Abstract only).
(Continued)

*Primary Examiner* — David J. McCrosky
(74) *Attorney, Agent, or Firm* — Clark & Elbing LLP

(57) ABSTRACT

Methods and devices to diagnose and treat male urinary incontinence and sexual dysfunction are provided. A multiple sensor-enabled catheter for rectal insertion in a male patient allows for the visualization and manipulation or positioning of the bladder. A multiple sensor-enabled catheter for rectal insertion in a male patient allows for the visualization and implementation of efficient and effective exercises to strengthen pelvic floor muscles.

10 Claims, 1 Drawing Sheet

Related U.S. Application Data continuation of application No. 14/580,708, filed on Dec. 23, 2014, now abandoned, which is a continuation-in-part of application No. 14/359,890, filed as application No. PCT/US2012/066613 on Nov. 27, 2012, now abandoned.

(60) Provisional application No. 61/563,889, filed on Nov. 28, 2011.

(52) U.S. Cl.
CPC .............. *A61B 5/208* (2013.01); *A61B 5/227* (2013.01); *A61B 5/4836* (2013.01); *A61B 5/6852* (2013.01); *A61B 5/6898* (2013.01)

(58) Field of Classification Search
CPC ...... A61M 2202/0496; A61M 2230/60; A61B 5/0036; A61B 5/202; A61B 5/4836; A61B 5/205; A61B 5/227; A61B 2562/0247; A61B 2562/043
See application file for complete search history.

(56) References Cited

U.S. PATENT DOCUMENTS

| | | |
|---|---|---|
| 4,669,478 A | 6/1987 | Robertson |
| 4,873,990 A | 10/1989 | Holmes et al. |
| D309,866 S | 8/1990 | Fukuda et al. |
| D310,275 S | 8/1990 | Su |
| 5,049,132 A | 9/1991 | Shaffer et al. |
| 5,328,077 A | 7/1994 | Lou |
| 5,386,836 A | 2/1995 | Biswas |
| 5,406,961 A | 4/1995 | Artal |
| 5,562,717 A | 10/1996 | Tippey et al. |
| 5,603,685 A | 2/1997 | Tutrone, Jr. |
| 5,674,238 A | 10/1997 | Sample et al. |
| 5,924,984 A | 7/1999 | Rao |
| 6,001,060 A | 12/1999 | Churchill et al. |
| 6,021,781 A | 2/2000 | Thompson et al. |
| 6,039,701 A | 3/2000 | Sliwa et al. |
| 6,056,699 A | 5/2000 | Sohn et al. |
| 6,080,118 A | 6/2000 | Blythe |
| 6,086,549 A | 7/2000 | Neese et al. |
| 6,264,582 B1 | 7/2001 | Remes |
| 6,272,371 B1 | 8/2001 | Shlomo |
| D458,681 S | 6/2002 | Sherlock et al. |
| 6,413,206 B2 | 7/2002 | Biswas |
| 6,432,037 B1 | 8/2002 | Eini et al. |
| 6,511,427 B1 | 1/2003 | Sliwa, Jr. et al. |
| 6,652,565 B1 | 11/2003 | Shimada et al. |
| 6,672,996 B2 | 1/2004 | Ross et al. |
| 6,679,854 B2 | 1/2004 | Honda et al. |
| 6,741,895 B1 | 5/2004 | Gafni et al. |
| D491,079 S | 6/2004 | Lim |
| D491,274 S | 6/2004 | Dubniczki et al. |
| 6,816,744 B2 | 11/2004 | Garfield et al. |
| 7,079,882 B1 | 7/2006 | Schmidt |
| 7,104,950 B2 | 9/2006 | Levy |
| D535,203 S | 1/2007 | Chen |
| D548,359 S | 8/2007 | Illein et al. |
| 7,577,476 B2 | 8/2009 | Hochman et al. |
| 7,608,037 B2 | 10/2009 | Levy |
| 7,628,744 B2 | 12/2009 | Hoffman et al. |
| 7,645,220 B2 | 1/2010 | Hoffman et al. |
| 7,736,298 B2 | 6/2010 | Guerquin et al. |
| 7,837,682 B2 | 11/2010 | Ostrovsky et al. |
| 7,892,179 B2 | 2/2011 | Rieth |
| 7,955,241 B2 | 6/2011 | Hoffman et al. |
| 7,957,794 B2 | 6/2011 | Hochman et al. |
| D651,531 S | 1/2012 | Rothman |
| 8,147,429 B2 | 4/2012 | Mittal et al. |
| 8,360,954 B2 | 1/2013 | Kim |
| 8,623,004 B2 | 1/2014 | Johnson et al. |
| 8,715,204 B2 | 5/2014 | Webster et al. |
| 8,728,140 B2 | 5/2014 | Feemster et al. |
| 8,740,767 B2 | 6/2014 | Rosen et al. |
| 8,751,003 B2 | 6/2014 | DiUbaldi et al. |
| 8,805,472 B2 | 8/2014 | Iglesias |
| 8,821,407 B2 | 9/2014 | Kirsner |
| 8,914,111 B2 | 12/2014 | Haessler |
| 8,983,627 B2 | 3/2015 | Pelger et al. |
| 9,155,885 B2 | 10/2015 | Wei et al. |
| 9,248,285 B2 | 2/2016 | Haessler |
| D759,813 S | 6/2016 | Newman et al. |
| D759,814 S | 6/2016 | Newman et al. |
| 9,381,351 B2 | 7/2016 | Haessler |
| 9,408,685 B2 | 8/2016 | Hou et al. |
| 9,656,067 B2 | 5/2017 | Pelger et al. |
| D800,898 S | 10/2017 | Sanders et al. |
| 9,861,316 B2 | 1/2018 | Egorov |
| 9,970,923 B2 | 5/2018 | Sturman et al. |
| 9,974,635 B2 | 5/2018 | Rosen et al. |
| D832,437 S | 10/2018 | Zeltwanger et al. |
| D841,155 S | 2/2019 | McMenamin et al. |
| D845,478 S | 4/2019 | Luke |
| D846,120 S | 4/2019 | Wallis et al. |
| D852,069 S | 6/2019 | Fu |
| D853,035 S | 7/2019 | Moretti |
| D855,825 S | 8/2019 | Parsons et al. |
| 10,470,862 B2 | 11/2019 | Iglesias |
| D877,895 S | 3/2020 | Sanders et al. |
| D888,949 S | 6/2020 | Beer et al. |
| D889,649 S | 7/2020 | Beer et al. |
| D893,026 S | 8/2020 | Leather |
| D896,958 S | 9/2020 | Beer et al. |
| D896,959 S | 9/2020 | Beer et al. |
| D897,530 S | 9/2020 | Beer et al. |
| D898,911 S | 10/2020 | Beer et al. |
| D899,593 S | 10/2020 | Beer et al. |
| D903,853 S | 12/2020 | Wiegerinck |
| D903,896 S | 12/2020 | Tianhao et al. |
| D908,160 S | 1/2021 | Sun |
| D909,679 S | 2/2021 | Chen |
| D910,851 S | 2/2021 | Lagrange et al. |
| D918,390 S | 5/2021 | Ollivier |
| D919,083 S | 5/2021 | Lee |
| D923,806 S | 6/2021 | Bunger von Wurmb et al. |
| D923,876 S | 6/2021 | Hasegawa |
| 11,135,085 B2 | 10/2021 | Mikkonen et al. |
| D938,581 S | 12/2021 | Floyd et al. |
| 11,266,343 B2 | 3/2022 | Iglesias |
| D956,229 S | 6/2022 | Beer et al. |
| D958,987 S | 7/2022 | Beer et al. |
| 11,426,625 B2 | 8/2022 | Iglesias et al. |
| 11,426,626 B2 | 8/2022 | Beer et al. |
| 2001/0001125 A1 | 5/2001 | Schulman et al. |
| 2001/0047132 A1 | 11/2001 | Johnson et al. |
| 2002/0022836 A1 | 2/2002 | Goble et al. |
| 2002/0111586 A1 | 8/2002 | Mosel et al. |
| 2002/0143275 A1* | 10/2002 | Sarvazyan ............ A61B 5/036 600/587 |
| 2003/0028180 A1 | 2/2003 | Franco |
| 2003/0087734 A1 | 5/2003 | Kring et al. |
| 2004/0236223 A1 | 11/2004 | Barnes et al. |
| 2004/0260207 A1 | 12/2004 | Eini et al. |
| 2005/0148447 A1 | 7/2005 | Nady |
| 2005/0177067 A1 | 8/2005 | Tracey et al. |
| 2005/0256423 A1 | 11/2005 | Kirsner |
| 2006/0036188 A1 | 2/2006 | Hoffman et al. |
| 2006/0074289 A1 | 4/2006 | Adler et al. |
| 2006/0084848 A1 | 4/2006 | Mitchnick |
| 2006/0211911 A1 | 9/2006 | Jao et al. |
| 2007/0066880 A1 | 3/2007 | Lee et al. |
| 2007/0232882 A1 | 10/2007 | Glossop et al. |
| 2007/0255090 A1 | 11/2007 | Addington et al. |
| 2007/0265675 A1 | 11/2007 | Lund et al. |
| 2007/0270686 A1 | 11/2007 | Ritter et al. |
| 2008/0077053 A1 | 3/2008 | Epstein et al. |
| 2008/0139876 A1 | 6/2008 | Kim |
| 2008/0146941 A1 | 6/2008 | Dala-Krishna |
| 2008/0149109 A1 | 6/2008 | Ziv |
| 2008/0154131 A1 | 6/2008 | Lee et al. |
| 2008/0171950 A1 | 7/2008 | Franco |

(56) References Cited

U.S. PATENT DOCUMENTS

| | | |
|---|---|---|
| 2008/0300658 A1 | 12/2008 | Meskens |
| 2009/0024001 A1 | 1/2009 | Parks et al. |
| 2009/0149740 A1 | 6/2009 | Hoheisel |
| 2009/0216071 A1 | 8/2009 | Zipper |
| 2009/0270963 A1 | 10/2009 | Pelger et al. |
| 2009/0306509 A1 | 12/2009 | Pedersen et al. |
| 2010/0069784 A1 | 3/2010 | Blaivas |
| 2010/0174218 A1 | 7/2010 | Shim |
| 2010/0222708 A1 | 9/2010 | Hitchcock et al. |
| 2010/0249576 A1 | 9/2010 | Askarinya et al. |
| 2010/0262049 A1 | 10/2010 | Novak et al. |
| 2010/0298895 A1 | 11/2010 | Ghaffari et al. |
| 2011/0054357 A1 | 3/2011 | Egorov et al. |
| 2011/0077500 A1 | 3/2011 | Shakiba |
| 2011/0144458 A1 | 6/2011 | Gauta |
| 2011/0190580 A1 | 8/2011 | Bennett et al. |
| 2011/0190595 A1 | 8/2011 | Bennett et al. |
| 2011/0196263 A1 | 8/2011 | Egorov et al. |
| 2012/0016258 A1 | 1/2012 | Webster et al. |
| 2012/0245490 A1 | 9/2012 | Fausett et al. |
| 2012/0265044 A1 | 10/2012 | Broens |
| 2012/0265049 A1 | 10/2012 | Iglesias |
| 2013/0035611 A1 | 2/2013 | White |
| 2013/0053627 A1 | 2/2013 | Bercovich et al. |
| 2013/0130871 A1 | 5/2013 | McCoy et al. |
| 2013/0144191 A1 | 6/2013 | Egorov et al. |
| 2013/0184567 A1 | 7/2013 | Xie et al. |
| 2013/0192606 A1 | 8/2013 | Ziv et al. |
| 2013/0237771 A1 | 9/2013 | Runkewitz et al. |
| 2013/0324380 A1 | 12/2013 | Horsley |
| 2014/0066813 A1 | 3/2014 | Daly et al. |
| 2014/0073879 A1 | 3/2014 | Cantor et al. |
| 2014/0088471 A1 | 3/2014 | Leivseth et al. |
| 2014/0155225 A1 | 6/2014 | Sedic |
| 2014/0213927 A1 | 7/2014 | Webster et al. |
| 2014/0275743 A1 | 9/2014 | Rosen et al. |
| 2014/0288612 A1 | 9/2014 | Addington et al. |
| 2014/0296705 A1 | 10/2014 | Iglesias |
| 2014/0309550 A1 | 10/2014 | Iglesias |
| 2015/0032030 A1 | 1/2015 | Iglesias |
| 2015/0112230 A1 | 4/2015 | Iglesias |
| 2015/0112231 A1 | 4/2015 | Iglesias |
| 2015/0133832 A1 | 5/2015 | Courtion et al. |
| 2015/0196802 A1 | 7/2015 | Siegel |
| 2015/0282763 A1 | 10/2015 | Rosenshein |
| 2016/0008664 A1 | 1/2016 | Siegel |
| 2016/0022198 A1 | 1/2016 | De Laat |
| 2016/0051354 A1 | 2/2016 | Patankar et al. |
| 2016/0074276 A1 | 3/2016 | Scheuring et al. |
| 2016/0121105 A1 | 5/2016 | Lee et al. |
| 2016/0279469 A1 | 9/2016 | Rose |
| 2016/0346610 A1 | 12/2016 | Iglesias et al. |
| 2017/0231709 A1 | 8/2017 | Gupta et al. |
| 2017/0281072 A1 | 10/2017 | Iglesias |
| 2017/0281299 A1 | 10/2017 | Iglesias |
| 2017/0291012 A1 | 10/2017 | Iglesias |
| 2017/0303843 A1 | 10/2017 | Iglesias |
| 2017/0312530 A1 | 11/2017 | Schilling et al. |
| 2017/0332959 A1 | 11/2017 | Bartlett |
| 2018/0021121 A1 | 1/2018 | Zeltwanger et al. |
| 2018/0146892 A1 | 5/2018 | Billard |
| 2018/0199816 A1 | 7/2018 | Kalt et al. |
| 2019/0133738 A1 | 5/2019 | Rosen et al. |
| 2019/0160332 A1 | 5/2019 | Beer et al. |
| 2020/0029812 A1 | 1/2020 | Govari et al. |
| 2020/0069161 A1 | 3/2020 | Schentag et al. |
| 2020/0146800 A1 | 5/2020 | Iglesias |
| 2020/0337888 A1 | 10/2020 | Beer et al. |
| 2020/0405142 A1 | 12/2020 | Whitaker |
| 2021/0069513 A1 | 3/2021 | Beer et al. |
| 2021/0106787 A1 | 4/2021 | Iglesias |
| 2021/0145353 A1 | 5/2021 | Iglesias |
| 2021/0161403 A1 | 6/2021 | Beer et al. |
| 2021/0321983 A1 | 10/2021 | Miyamoto |
| 2021/0353195 A1 | 11/2021 | Beer et al. |
| 2023/0201659 A1 | 6/2023 | Iglesias et al. |
| 2023/0201660 A1 | 6/2023 | Bohorquez et al. |
| 2023/0225847 A1 | 7/2023 | Iglesias |

FOREIGN PATENT DOCUMENTS

| | | |
|---|---|---|
| CN | 103622710 A | 3/2014 |
| CN | 204839545 U | 12/2015 |
| DE | 10345282 B3 | 4/2005 |
| DE | 2020/18103016 U1 | 6/2018 |
| EP | 0268972 A2 | 6/1988 |
| EP | 1105040 A1 | 6/2001 |
| EP | 1231859 A1 | 8/2002 |
| EP | 2429626 A2 | 3/2012 |
| EP | 2689724 A1 | 1/2014 |
| EP | 2809231 A4 | 9/2015 |
| EP | 3366212 A1 | 8/2018 |
| GB | 2492754 A | 1/2013 |
| JP | 2002-143133 A | 5/2002 |
| JP | 2008-532578 A | 8/2008 |
| JP | 2009-538176 A | 11/2009 |
| JP | 2011-183167 A | 9/2011 |
| RU | 2307636 C1 | 10/2007 |
| WO | WO-96/05768 A1 | 2/1996 |
| WO | WO-99/05963 A1 | 2/1999 |
| WO | WO-00/09013 A1 | 2/2000 |
| WO | WO-00/23030 A1 | 4/2000 |
| WO | WO-01/37732 A1 | 5/2001 |
| WO | WO-02/17987 A2 | 3/2002 |
| WO | WO-2006/107930 A2 | 10/2006 |
| WO | WO-2007/136266 A1 | 11/2007 |
| WO | WO-2010/131252 A2 | 11/2010 |
| WO | WO-2011/050252 A1 | 4/2011 |
| WO | WO-2011/121591 A2 | 10/2011 |
| WO | WO-2011/159906 A2 | 12/2011 |
| WO | WO-2012/079127 A1 | 6/2012 |
| WO | WO-2012/138232 A1 | 10/2012 |
| WO | WO-2013/082006 A1 | 6/2013 |
| WO | WO-2013/115310 A1 | 8/2013 |
| WO | WO-2013/116310 A1 | 8/2013 |
| WO | WO-2015/103629 A1 | 7/2015 |
| WO | WO-2016/026914 A2 | 2/2016 |
| WO | WO-2016/042310 A1 | 3/2016 |
| WO | WO-2016/067023 A1 | 5/2016 |
| WO | WO-2016/119002 A1 | 8/2016 |
| WO | WO-2016/203485 A1 | 12/2016 |
| WO | WO-2017/149688 A1 | 9/2017 |
| WO | WO-2018/023037 A1 | 2/2018 |
| WO | WO-2019/084468 A1 | 5/2019 |
| WO | WO-2019/084469 A1 | 5/2019 |
| WO | WO-2019/200222 A1 | 10/2019 |
| WO | WO-2019/210204 A1 | 10/2019 |
| WO | WO-2020/092343 A1 | 5/2020 |

OTHER PUBLICATIONS

*Gray's Anatomy, 39th Edition*, Churchill Livingstone, p. 1290, definition of "Bladder neck" (2005) (3 pages).

Kandadai et al., "Correct Performance of Pelvic Muscle Exercises in Women Reporting Prior Knowledge," Female Pelvic Med Reconstr Surg. 21(3):135-40 (2015).

Malcovati et al., Interface Circuitry and Microsystems. *MEMS—A Practical Guide to Design, Analysis, and Applications*. Jan G. Korvink and Oliver Paul, 901-942 (2006).

Moen et al., "Pelvic floor muscle function in women presenting with pelvic floor disorders," Int Urogynecol J Pelvic Floor Dysfunct. 20(7):843-6 (2009).

Nygaard et al., "Efficacy of pelvic floor muscle exercises in women with stress, urge, and mixed urinary incontinence," Am J Obstet Gynecol. 174(1 Pt 1):120-125 (1996) (Abstract only).

Parekh et al., "The role of pelvic floor exercises on post-prostatectomy incontinence," J Urol. 170(1):130-33 (2003) (Abstract Only) (2 pages).

Rosenbaum, "Pelvic floor involvement in male and female sexual dysfunction and the role of pelvic floor rehabilitation in treatment: a literature review," J Sex Med. 4(1):4-13 (2007) (Abstract only) (2 pages).

(56) References Cited

OTHER PUBLICATIONS

Rosenbaum et al., "The Role of Pelvic Floor Physical Therapy in the Treatment of Pelvic and Genital Pain-Related Sexual Dysfunction," J Sex Med. 5(3): 513-23 (2008).
Rosenblatt et al., "Evaluation of an accelerometer-based digital health system for the treatment of female urinary incontinence: A pilot study," Neurourol Urodyn. 38(7): 1944-1952 (2019).
Rosenblatt et al., "Interactive Pelvic Floor Muscle Training for Female Urinary Incontinence," Renovia, Inc., retrieved Apr. 30, 2019 from <renoviainc.com/wp-content/uploads/2018/04/REN005.01-White-Paper-12Apr18-FINAL.pdf> (2018) (6 pages).
*Stedman's Medical Dictionary, 28th Edition*, Lippincott Williams & Wilkins (LWW), p. 2072 (2006) (3 pages).
First Examination Report for Australian Patent Application No. 2017245476, dated Sep. 12, 2018 (3 pages).
First Office Action for Mexican Patent Application No. MX/a/2014/006219, dated Jul. 31, 2017 (7 pages).
Examination Report for Canadian Patent Application No. 2,856,724, dated Oct. 18, 2018 (3 pages).
Extended European Search Report for European Patent Application No. 17203166.8, dated Jul. 31, 2018 (10 pages).
Communication pursuant to Article 94(3) EPC for European Patent Application No. 12852598.7, dated Jun. 6, 2018 (4 pages).
First Examination Report for Australian Patent Application No. 2018200715, dated Jun. 26, 2018 (4 pages).
International Preliminary Report on Patentability for International Application No. PCT/US2017/044444, mailed Feb. 7, 2019 (14 pages).
International Search Report and Written Opinion for International Application No. PCT/US17/44444, mailed Oct. 19, 2017 (21 pages).
International Search Report and Written Opinion for International Application No. PCT/US18/57811, mailed Jan. 29, 2019 (18 pages).
International Search Report and Written Opinion for International Application No. PCT/US2019/029400, mailed Jul. 10, 2019 (17 pages).
International Search Report and Written Opinion for International Application No. PCT/US2019/027168, mailed Aug. 12, 2019 (39 pages).
International Search Report and Written Opinion for International Application No. PCT/US2012/066613, mailed Feb. 6, 2013 (5 pages).
Second Examination Report for Canadian Patent Application No. 2,862,928, dated Nov. 20, 2018 (5 pages).
Summons to attend oral proceedings pursuant to Rule 115(1) EPC, issued on Aug. 3, 2017 by the European Patent Office related to the European Patent Application No. 13743383.5 (10 pages).
International Search Report and Written Opinion for International Application No. PCT/US2019/058527, mailed Feb. 21, 2020 (18 pages).
Office Action for Japanese Patent Application No. 2019-504938, dated May 18, 2021 (10 pages).
International Search Report and Written Opinion for International Application No. PCT/US2021/033155, mailed Aug. 25, 2021 (19 pages).
Communication pursuant to Article 94(3) EPC for European Patent Application No. 15733078.8, dated Aug. 24, 2021 (8 pages).
Office Action for Japanese Patent Application No. 2020-143711, dated Sep. 8, 2021 (4 pages).
First Examination Report for Australian Patent Application No. 2020281099, dated Nov. 2, 2021 (6 pages).
Office Action for Brazilian Patent Application No. BR112019001746-1, dated Dec. 10, 2021 (5 pages).
Extended European Search Report for European Patent Application No. 19793343.5, dated Jan. 27, 2022 (7 pages).
Notice of Preliminary Rejection for Korean Patent Application No. 10-2019-7005863, dated Jan. 26, 2022 (17 pages).
Office Action for Chinese Patent Application No. 201780060078.4, issued Jan. 17, 2022 (20 pages).
Office Action for Japanese Patent Application No. 2019-504938, dated Feb. 8, 2022 (13 pages).
Office Action for Chinese Patent Application No. 201880083895.6, dated Feb. 8, 2022 (24 pages).
Extended European Search Report for European Patent Application No. 19786241.0, dated Apr. 29, 2022 (10 pages).
Notice of Reasons for Refusal for Japanese Patent Application No. 2020-143711, mailed May 9, 2022 (7 pages).
Office Action for Chinese Patent Application No. 201780060078.4, issued Apr. 13, 2022 (19 pages).
Extended European Search Report for European Patent Application No. 19878836.6, dated Jun. 1, 2022 (7 pages).
Office Action for Canadian Patent Application No. 2,936,061, dated Jun. 23, 2022 (4 pages).
Notice of Last Preliminary Rejection for Korean Patent Application No. 10-2019-7005863, dated Jul. 28, 2022 (4 pages).
Office Action for Brazilian Patent Application No. BR112020008231-7, dated Sep. 7, 2022 (5 pages) (Informal translation of Office Action included).
Extended European Search Report dated Aug. 16, 2017 issued in related EP Application No. 15733078.8 filed Aug. 2, 2016 (6 pages).
International Search Report and Written Opinion, dated Mar. 26, 2015, issued in International Application No. PCT/US2015/010356, filed on Jan. 6, 2015 (5 pages).
Office Action for Chinese Patent Application No. 201880083895.6 dated Oct. 25, 2022 (8 pages).
Office Action for European Patent Application No. 17203166.8, dated Aug. 29, 2023 (6 pages).

* cited by examiner

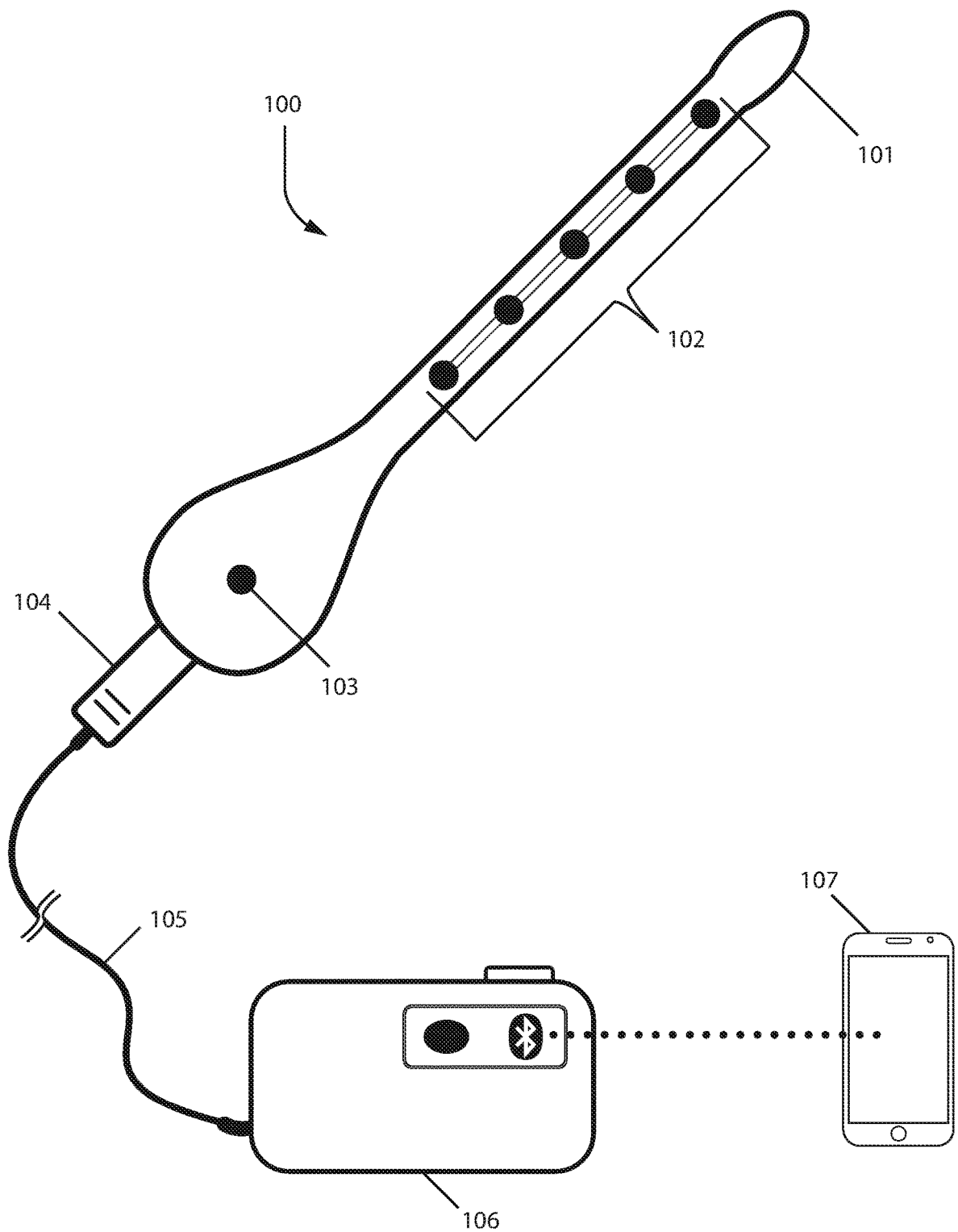

TREATMENT OF MALE URINARY INCONTINENCE AND SEXUAL DYSFUNCTION

CROSS-REFERENCE TO RELATED APPLICATIONS

This application is a continuation of U.S. patent application Ser. No. 14/580,708, filed Dec. 23, 2014, which is a continuation-in-part application of U.S. patent application Ser. No. 14/359,890, entitled "Treatment of Urinary Incontinence," filed May 21, 2014, which claims priority to international patent application PCT/US2012/066613, filed Nov. 27, 2012, and U.S. provisional Patent Application No. 61/563,889, filed Nov. 28, 2011, the entirety of which are incorporated herein by reference for all purposes.

BACKGROUND

The present embodiments relate to the devices, diagnosis, and treatment of male urinary incontinence and sexual dysfunction. The diagnosis and treatment may involve the use of a multiple sensor-enabled catheter capable of providing real-time data regarding the patient's anatomy and physiology, such as muscular function of the pelvic floor and rectal sphincter, as well as the position and movement of the catheter within the patient.

Human males may experience urinary incontinence (UI), which is the unintentional loss (accidental leakage) of urine; as well as sexual dysfunction, which is a problem during the phase of the sexual response cycle that prevents the man or couple from experiencing satisfaction from sexual activity. Reports indicate that urinary incontinence can occur in 11% of the male population whereas male sexual dysfunction can occur in 31% of the male population. Weak or damaged pelvic floor muscles (hypotonia), overactive pelvic floor muscles (hypertonia), certain prostate conditions, and nerve damage are some of the possible underlying causes of urinary incontinence in men. Different types of urinary incontinence in men include stress incontinence, urge incontinence, and overflow incontinence. Some men may experience more than one type of incontinence. Diagnosis of urinary incontinence in men typically involves a medical history and physical exam, and may include keeping a bladder diary. Diagnosis may also include an ultrasound and urodynamic testing. Therapy for urinary incontinence in men may include behavioral modification such as like bladder training and Kegel exercises, medication, surgery, or a combination of these therapies.

Sexual dysfunction is the inability to have satisfactory sexual activity. This definition depends on each person's own interpretation of satisfactory sexual activity. Typically, male sexual dysfunction includes erectile dysfunction (ED, or impotence), and ejaculation problems such as premature ejaculation. ED is the inability to acquire or maintain a satisfactory erection. The prevalence of erectile dysfunction varies according to the patient's age. About 18% of men from 50 to 59 years of age and 37% of those aged 70 to 75 years will suffer from erectile dysfunction. Ejaculation problems involve the improper discharge of sperm, prostatic, and seminal vesicle fluid through the urethra. Premature ejaculation is the most common of the ejaculatory disorders; approximately 20% to 30% of men will have premature ejaculation. As with incontinence, sexual dysfunction in males is often associated with, or caused by, pelvic floor dysfunction.

Pelvic floor muscle training (PFMT, or Kegel exercises), includes a series of exercises designed to rehabilitate the musculature of the pelvic floor. For example, PFMT can help strengthen and tone the muscles under the bladder, and bowel (large intestine), and thus aid those who have problems with urine leakage, bowel control or sexual dysfunction. A current problem with PFMT is that the individual is often unable to visualize or attain the proper muscle position and control to carry out an efficient and effective exercise regimen required to rehabilitate the pelvic floor muscles.

SUMMARY

The embodiments described herein relate to the diagnosis and treatment of male UI and male sexual dysfunction. In one embodiment, diagnosis and treatment involves the use of a multiple sensor-enabled catheter capable of providing real-time data regarding the patient's anatomy and physiology, such as muscular function of the rectal sphincter or pelvic floor, as well as the position and movement of the catheter within the patient. In one embodiment, the device may be a pressure sensor-enabled catheter.

In one embodiment, the multiple sensor-enabled catheter may include at least one sensor capable of providing real-time data of one or more types selected from the group consisting of position, movement, pressure, and flow. In this regard, a sensor may have a single measurement and reporting capability, or may have multiple measurement and reporting capabilities.

The present embodiments also provide for methods for the diagnosis or treatment of male UI, comprising positioning a multiple sensor-enabled catheter in a male patient's rectum and determining the anatomical state of the patient, which treatment is capable of relieving or ameliorating incontinence. The anatomical state may be the relative position of the bladder neck and urethra. The anatomical state may also be the sphincteric and supportive functions of the pelvic floor. The method of diagnosis or treatment may also include manipulating the patient to relieve the incontinence. The manipulation may be performed by the health care provider or the patient. The manipulation may include achieving a particular anatomical position of the bladder neck relative to the urethra or achieving a particular muscular function of the pelvic floor.

The present embodiments also include a method for the diagnosis or treatment of male sexual dysfunction, comprising positioning a multiple sensor-enabled catheter in a male patient's rectum and determining the anatomical state of the patient, which treatment is capable of relieving or ameliorating a sexual dysfunction. For example, the treatment if capable of achieving efficient and effective control of pelvic floor muscles to relieve the sexual dysfunction.

The present embodiments contemplate the real-time position and movement tracking as described in U.S. Pat. No. 8,805,472. In this regard, the real-time position and movement tracking may include sensing the position of the bladder relative to a fixed reference point within the patient's body, by providing a catheter enabled with a sensor and capable of providing positional or movement data. The fixed reference point within the body may be the pubic bone, the coccyx, the bladder, the urethra, the prostate, or the rectum. The method may be performed in real-time, for example, during an operation. In another embodiment, the method may be performed at multiple time intervals. The multiple time intervals may occur, for example, pre- and post-event, wherein the event may be injury or surgery.

BRIEF DESCRIPTION OF THE DRAWINGS

FIG. 1 depicts a view of an example probe device comprising a multiple sensor-enabled catheter.

DETAILED DESCRIPTION

All patents, applications, and other publications identified are expressly incorporated herein by reference for the purpose of describing and disclosing, for example, the devices methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless clearly indicated otherwise by context. Throughout this specification and claims, unless otherwise indicated, "comprise," "comprises" and "comprising" are used inclusively rather than exclusively. The term "or" is inclusive unless modified, for example, by "either." Other than in the operating examples, or where otherwise indicated, all numbers should be understood as modified in all instances by the term "about."

Unless otherwise defined, scientific and technical terms used herein shall have the meanings that are commonly understood by those of skill in the art. The terminology used herein is for the purpose of describing particular embodiments only, and is not intended to limit the scope of the present invention, which is defined solely by the claims.

One embodiment described herein provides for methods for the diagnosis or treatment of male urinary incontinence, comprising positioning in the rectum of a male patient a multiple sensor-enabled catheter, visualizing the anatomical state of the patient, and manipulating the patient's body to a position capable of relieving the incontinence. In an additional embodiment, the anatomical state is the relative position of one or more internal anatomical reference points selected from the pubic bone, the coccyx, the bladder, the urethra, the prostate, and the rectum. In one other embodiment, the anatomical state is the muscular function of the bladder or rectal sphincter.

Another embodiment described herein provides for methods for the diagnosis or treatment of male sexual dysfunction, comprising positioning in the rectum of a male patient a multiple sensor-enabled catheter, visualizing the anatomical state of the patient, and manipulating the patient's body to a position capable of strengthening pelvic floor muscles. In an additional embodiment, the male sexual dysfunction is erectile dysfunction or premature ejaculation.

An additional embodiment provides for a method of rehabilitating the pelvic floor musculature, comprising positioning in the rectum of a male patient a multiple sensor-enabled catheter and visualizing the anatomical state of the patient, wherein the patient manipulates the catheter as a method of exercising control of sphincter or pelvic floor muscles.

In the present embodiments, for example, a catheter is enabled with at least one sensor capable of providing real-time data of at least one data type selected from the group consisting of position, movement, pressure, and flow. In this regard, a sensor may have a single measurement and reporting capability, or may have multiple measurement and reporting capabilities. The data obtained by the multiple sensor-enabled catheter may be reported in any number of ways know in the art, including the transmission to, and visualization on, a graphical user interface. For purposes of the embodiments, "real-time" may include instantaneous as well as delayed observation, reporting, or recording of an event as it elapses.

Advantageously, by viewing a real-time image of where the bladder and urethra are located in a patient relative to one or more other anatomical reference points during a procedure, a health care provider may manipulate the patient such that the patient's bladder and the urethra are in a position capable of relieving or ameliorating incontinence. In other instances, a patient himself may visualize his own anatomical state using the multiple sensor-enabled catheter, and may manipulate his body such that his bladder and the urethra are in a position capable of relieving incontinence. Additionally, the patient himself may visualize his anatomical state using the multiple sensor-enabled catheter, and may manipulate his body to a position capable of controlling his pelvic floor muscles to relieve incontinence.

In addition, by viewing a real-time image of where the bladder and urethra are located in a patient relative to one or more other anatomical reference points during a procedure, a health care provider may manipulate the patient such that the patient is in a position capable of strengthening his pelvic floor muscles. In other instances, the patient himself may visualize his anatomical state using the multiple sensor-enabled catheter, and may manipulate his body to a position capable of strengthening his pelvic floor muscles. In either instance, the visualization allows the health care provider or the male patient to achieve the efficient and effective exercising of his pelvic floor muscles to control pelvic floor musculature and relieve sexual dysfunction.

A multiple sensor-enabled catheter provides a valuable study or diagnostic tool for a health care provider as well as a patient, particularly when the patient is considering surgery that may result in UI or sexual dysfunction as a side effect or post-surgical complication. For example, a health care provider may provide the patient with an in-office procedure that determines a baseline position or relative mobilization of the bladder (baseline), before possible damage to his pelvic floor that might occur, for example, during prostate or colorectal surgery; such that if surgical repair is subsequently performed, his bladder can be repositioned to the original, pre-incontinence anatomic position. Surgery could also be performed on patients with a surgically correctable structural defect, using the multiple sensor-enabled catheter to provide positioning data. Such procedures may involve a male sling, placement of an artificial bladder sphincter, bulking, or ultimately urinary diversion.

A multiple sensor-enabled catheter can also be used as a diagnostic tool where the position of the bladder needs to be adjusted surgically to correct a urinary problem, such as that involving male prostactic hypertrophy causing a stricture of the urethra. The multiple sensor-enabled catheter may also be used after male prostatectomy to help determine the optimal positioning of the urethra and bladder neck, or the pressure exerted by the bladder sphincter. Another use for a multiple sensor-enabled catheter would be to correct male fecal incontinence The multiple sensor-enabled catheter may incorporate at least one sensor capable of measuring or reporting data of various types, including position, movement, pressure, or flow. A multiple sensor-enabled catheter with more than one individual sensor may be arrayed as depicted in FIG. 1, or it may incorporate a single sensor that has multiple measurement and reporting capabilities.

The position or movement data may be of the sort measured or reported by any number of sensor devices, including accelerometer, gyroscope, inductive non-contact position sensor, string potentiometer, linear variable differential transformer, potentiometer, capacitive transducer, Eddy-current sensor, Hall effect sensor, optical proximity sensor, piezo-electric transducer, or photodiode array sensor devices. The position or movement data may also include magnetic, electromagnetic, microelectromechanical, radio frequency, ultrasound, or video data.

The pressure or flow data may be of the sort measured or reported by any number of sensor devices, including force collector types, such as piezo-resistive, capacitive, electromagnetic, piezo-electric, optical, potentiometric, or other types, such as resonant, thermal, ionization, ultrasonic, or density (mass and index of refraction) sensor devices.

For example, an embodiment of a multiple sensor enabled catheter comprising a firm tip, which may be about ½ inch in length to guide the catheter through the rectum. The number and precise placement of an individual sensor may vary depending on the type of positional, movement, pressure or flow measurement or reporting system employed. An individual sensor may have a single function or be multi-function (such as positional tracking combined with pressure and flow sensing). The multiple sensor-enabled catheter may also embody a video observation or recording device as well as an illumination source to facilitate such video capture. The precise placement of the sensor(s) and video capture component(s) are not pre-defined, and may be configured according to the requirements of the desired application.

EXAMPLES

As described herein, catheters useful in the present embodiments may embody at least one sensor capable of measuring and reporting at least one data type, including position, movement, pressure, and flow. These include, but are not limited to, magnetic, electromagnetic, microelectromechanical, radio frequency, ultrasound, and video. One example of a multiple sensor-enabled catheter, as shown in FIG. 1, is a probe or catheter 100 containing multiple sensors arranged in an array 102. The probe or catheter 100 may be constructed of a silicon or other material suitable for medical use in or on a patient's body. The probe or catheter 100 may include a distal probe or catheter tip 101, which may be constructed of a material with sufficient hardness or rigidity to facilitate the ease of insertion of the probe or catheter 100 into a patient's rectum. The probe or catheter 100 may also contain a proximal portion with a connector/handle 104 to facilitate positioning or movement of the probe or catheter 100 by the patient or health care provider. A sensor, such as a pressure sensor 103, may be contained in the proximal portion of the probe or catheter 100 to facilitate the assessment of rectal sphincter strength and/or control when the probe or catheter 100 is inserted into the patient's rectum.

In other embodiments, the sensor(s) may be positioned in the probe or catheter 100 without a particular spatial relationship to any other sensor(s). The probe or catheter 100 may contain a microelectromechanical (MEMS) device(s), a 3-axis accelerometer, a roll/pitch gyroscope and a yaw rate gyroscope, and a pressure and flow transducer. The devices may also be mounted on a small flexible printed circuit board (PCB) and then attached to the probe or catheter. The 3-axis accelerometer may track translation of the probe or catheter in three directions. The gyroscopes are utilized to account for gravitational rotation, allowing real-time movement to be tracked.

In one embodiment, a PCB may be prepared with the three MEMS devices mounted thereon. Soft leads trail the MEMS devices to supporting devices, including, for example, a data acquisition card which may be used for transforming analog signals to digital signals. The PCB is set within the wall of the probe or catheter. The location of the probe or catheter may be determined by the output signals of the MEMS devices.

The multiple sensor enabled catheter may be linked via data cable 105 to a transmitter 106, which can provide a wireless data signal (such as BLUETOOTH® ) to a device 107 (computer, tablet, smartphone, or similar device) capable of receiving the transmission of data collected by the sensors. The connection of the data cable 105 to the catheter or probe 100 may be achieved through a mating interface with connector/handle 104. Alternatively, the transmitter may be contained within the probe/catheter or the probe/catheter handle. The linked device 107 may process the data or provide a graphical user display, or transmit such information to another device(s) to accomplish similar tasks. In another embodiment, the probe or catheter 100 may transmit a wireless data signal directly to the device 107.

The patient may be asked to recreate maneuvers that induce incontinence at the same time that the parameters for the location/pressure/flow/visualization of the urethra and bladder are determined.

The urethra and bladder are manipulated to the position where muscular pressure is optimized and urine flow is returned to normal physiological control. These positions for the urethra and bladder neck may be displayed in real-time on a graphical user interface and/or recorded.

In the case of surgical intervention, if no pre-incontinence position is known, the urethra and bladder neck are positioned based on data collected from a cohort of patients with similar UI history or profile. Where pre-incontinence data is available (e.g., the positions of the urethra and bladder neck are based on patient information from an earlier date), then at the time of surgery the urethra and bladder neck are repositioned to the location where the patient was previously determined to be continent.

Following examination using the multiple sensor-enabled catheter, a health care provider may conclude that rehabilitation is an efficacious option for the patient. In this regard, the measurements provided by the multiple sensor-enabled catheter may be recorded to facilitate appropriate patient instructions on performing Kegel exercises in an optimal manner using the visual (on-screen) information provided by the catheter in real-time. Once engaging the proper musculature has been successfully communicated to a patient during a medical office visit, the patient may be sent home with the instructions to perform Kegel exercises five to six times daily, for example. Four to six weeks later the patient may return for another examination using the multiple sensor-enabled catheter to evaluate rehabilitative treatment effectiveness, which may allow a health care provider to advise the patient about the prospects for restoring complete continence or alleviating sexual dysfunction with a continued rehabilitation regime or a surgical procedure.

Detailed embodiments are disclosed herein; however, it is to be understood that the disclosed embodiments are merely exemplary of the claimed invention that may be embodied in various forms. It will be appreciated that many modifications and other variations that will be appreciated by those skilled in the art are within the intended scope of this invention as claimed below without departing from the teachings, spirit, and intended scope of the invention.

What is claimed is:

1. A method for diagnosing or treating urinary incontinence in a subject comprising:
   a) inserting into a rectum of the subject a device comprising a handle and a probe configured to enter the rectum, wherein the probe comprises microelectromechanical (MEM) accelerometers positioned along a length of the probe and wherein the device lacks accelerometers in the handle,
   b) determining and visualizing on a graphical user interface a position of the accelerometers of the probe as a representation of an anatomical position of a bladder, bladder neck, or urethra of the subject in real-time, and
   c) manipulating the anatomical position of the bladder, bladder neck, or urethra relative to at least one fixed anatomical reference point selected from the group consisting of a pubic bone, a coccyx, a bladder, a urethra, a prostate, and a rectum, thereby diagnosing or relieving the incontinence.

2. The method of claim 1, wherein the anatomical position of the subject is transmitted in real-time as wireless data to the graphical user interface.

3. The method of claim 1, wherein the anatomical position of the bladder neck and the urethra is transmitted in real-time as wireless data to the graphical user interface.

4. The method of claim 1, wherein the method further comprises determining a muscular function of a bladder sphincter, a rectal sphincter, or a pelvic floor muscle of the subject.

5. The method of claim 4, wherein the muscular function is determined by having the subject manipulate the pelvic floor muscle.

6. The method of claim 1, wherein the device is a catheter.

7. The method of claim 1, wherein the manipulating comprises having the subject perform a pelvic floor muscle exercise.

8. The method of claim 7, wherein the pelvic floor muscle exercise is repeated one or more times.

9. The method of claim 1, wherein the manipulating comprises performing an exercise that strengthens a sphincter of the subject.

10. The method of claim 1, wherein the device further comprises one or more pressure sensors.

* * * * *